(12) United States Patent
Gan et al.

(10) Patent No.: US 7,646,170 B2
(45) Date of Patent: Jan. 12, 2010

(54) METHOD OF SELECTING REPLACEMENT INDICATING VOLTAGE FOR AN IMPLANTABLE ELECTROCHEMICAL CELL

(75) Inventors: Hong Gan, Williamsville, NY (US); Robert Rubino, Williamsville, NY (US); Yuemin Zhang, Clarence Center, NY (US); Esther Takeuchi, East Amherst, NY (US)

(73) Assignee: Greatbatch Ltd., Clarence, NY (US)

( * ) Notice: Subject to any disclaimer, the term of this patent is extended or adjusted under 35 U.S.C. 154(b) by 762 days.

(21) Appl. No.: 11/382,744

(22) Filed: May 11, 2006

(65) Prior Publication Data

US 2007/0262751 A1 Nov. 15, 2007

(51) Int. Cl.
*H01M 10/44* (2006.01)
(52) U.S. Cl. ........................... 320/130; 320/132
(58) Field of Classification Search ................. 320/103, 320/107, 112, 116, 124, 125, 128, 130, 132, 320/134, 136; 429/12, 90, 209, 231.1
See application file for complete search history.

(56) References Cited

U.S. PATENT DOCUMENTS 6,936,379 B2  8/2005  Gan et al.
2003/0134200 A1 *  7/2003  Tanaka et al. ............ 429/231.1
2006/0093914 A1 *  5/2006  Tanaka et al. ............ 429/231.1
2007/0009773 A1 *  1/2007  Xie ............................ 429/13

* cited by examiner

Primary Examiner—Edward Tso
(74) Attorney, Agent, or Firm—Michael F. Scalise

(57) ABSTRACT

A method for providing an elective replacement indicator (ERI) voltage for a first implantable electrochemical cell, comprising the steps of providing a second, substantially identical exemplary electrochemical cell; repeatedly connecting and disconnecting the second cell to a sequence of at least three loads, thereby discharging the second cell from a state of about zero percent to at least about ninety percent depth-of-discharge; generating cell voltage vs. depth-of-discharge plots for the at least three loads repeatedly connected to the second cell; identifying a range of depth-of-discharge for the at least three loads wherein a statistical indicator of the second cell voltage variability with load at the same depth-of-discharge is less than a predetermined value among the at least three loads; and then defining the ERI voltage for the first implantable electrochemical cell as the voltage that occurs at a predetermined load at a specified point within the identified range for the second electrochemical cell.

4 Claims, 4 Drawing Sheets

METHOD OF SELECTING REPLACEMENT INDICATING VOLTAGE FOR AN IMPLANTABLE ELECTROCHEMICAL CELL

BACKGROUND OF THE INVENTION

1. Field of the Invention

The present invention relates generally to an electrochemical cell to be used for a high reliability application such as an implantable medical device. The cell of the present invention is particularly useful in an implantable medical device such as a cardioverter defibrillator or pacemaker. In such an application, it is critical to be able to provide a clear indication that the cell is approaching end-of-life. The cell can thus be replaced prior to its being unable to adequately power the device, which could result in loss of device function. More particularly, the present invention relates in one embodiment to a method for selecting the optimal replacement voltage of an electrochemical cell.

2. Description of Related Art

A currently preferred power source for an implantable medical device is an alkali metal electrochemical cell, such as of lithium coupled with a sandwich cathode. The sandwich cathode design comprises a second cathode active material of a relatively high energy density but of a relatively low rate capability sandwiched between two current collectors with a first cathode active material having a relatively low energy density but of a relatively high rate capability in contact with the opposite sides of the current collectors.

A number of patents and publications have disclosed such electrochemical cells. For example, U.S. Pat. No. 6,551,747 to Gan, which is assigned to the assignee of the present invention and incorporated herein by reference, describes a sandwich cathode design having a second cathode active material of a relatively high energy density but of a relatively low rate capability sandwiched between two current collectors and with a first cathode active material having a relatively low energy density but of a relatively high rate capability in contact with the opposite sides of the two current collectors. A preferred anode is lithium (Li), a preferred first cathode material is silver vanadium oxide (SVO) and a preferred second cathode material is carbon monofluoride ($CF_x$).

U.S. Pat. No. 6,926,991 to Gan et al., which is assigned to the assignee of the present invention and incorporated herein by reference, discloses a cathode design having a first cathode active material of a relatively low energy density but of a relatively high rate capability contacted to a first cathode current collector and a second cathode active material having a relatively high energy density but of a relatively low rate capability in contact with a second cathode current collector. The first and second cathode current collectors are connected to a common terminal lead. The preferred cell materials are also Li/SVO/$CF_x$.

The present invention provides an early warning indicator as to when the cell's discharge capacity is nearing end-of-life (EOL) based on empirical observations of the discharge efficiency of the first and second cathode active materials. This early warning is defined as the elective replacement indicator (ERI) and signals a physician when it is time to replace the medical device. Suitable medical devices include cardiac defibrillators, neurostimulators, pacemakers, and the like.

Because an implantable electrochemical cell often supports such a life-sustaining device in a patient, it is critical to be able to identify the point at which the cell needs to be replaced before it is no longer functional. This gives the physician and patient time to replace the battery without jeopardizing the therapeutic function of the device. Typically, the replacement indicator is based on the potential of the cell under some defined load.

Historically, the Li/SVO cell system has been used as the power source for implantable cardiac defibrillator applications requiring high rate pulse capability, i.e., about 1 to about 4 amps. Since Li/SVO cells have a staged discharge voltage profile, a pre-determined background voltage is generally used as the ERI. This pre-determined voltage value varies depending on the cell size, theoretical capacity and the associated device design. Additionally, due to the characteristic voltage delay and growth in resistance under direct current (Rdc) that occurs at about the 2.6-volt plateau, a pre-determined Rdc or voltage value under high current pulsing is sometimes used as an ERI. Consequently, the ERI selection has heretofore been complicated and dependent on the individual device design of each cell manufacturer.

In general, the elective replacement indicator voltage should be chosen near the end of the cell's useable capacity, in order to maximize the lifetime of the cell. In one commonly used method of determining cell replacement indicating voltage, the capacity of the cell that is useable by the device is calculated and then the capacity required to give an adequate time for replacement is subtracted. The remaining cell capacity is considered the capacity available prior to replacement and can be correlated with a replacement voltage under a given load. Since the voltage of the cell is load dependent, this methodology can be problematic. Under a heavy load, the replacement indicating voltage will be reached sooner, resulting in a reduction in apparent device lifetime. Alternatively, under a light load, the replacement indicating voltage will be reached later. This results in a reduction in time for replacement prior to loss of device function, and higher risk to the patient.

U.S. Pat. No. 6,926,991 to Gan et al., which is assigned to the assignee of the present invention and incorporated herein by reference, describes a method for providing a physician with an elective replacement indicator for an implantable medical device. The medical device is powered by an electrochemical cell having a lithium anode coupled to a sandwich cathode comprising the configuration SVO/current collector/$CF_x$, with the SVO facing the anode. The indicator is predicated on when the cell's discharge capacity is nearing end-of-life (EOL) based on the theoretical capacity and the discharge efficiency of the SVO and $CF_x$ active materials, which serves as an indicator of when it is time to replace the medical device. Gan et al. provide a mechanism for determining both EOL and ERI by varying the relative weight of SVO to $CF_x$ in a cathode having one of the following configurations: SVO/current collector/$CF_x$/current collector/SVO, SVO/current collector/SVO/$CF_x$/SVO/current collector/SVO, SVO/current collector/$CF_x$ with the SVO facing the anode, and SVO/current collector/SVO/$CF_x$ with the SVO facing the anode.

In use with a device to be powered, a cell may be subject to numerous transient perturbations such as a series of high current pulses. After a perturbation, the cell voltage will be artificially lowered until concentration gradients within the cell have relaxed. If the cell voltage is sampled too soon after a perturbation, the replacement indicating voltage could be prematurely indicated, reducing the lifetime of the cell. Alternatively, if the device is programmed to wait an excessive amount of time after a perturbation to begin monitoring voltage relative to the replacement indicator, the replacement indicating voltage could be indicated late, resulting in too short a time for cell replacement prior to loss of device function.

SUMMARY OF THE INVENTION

It is an object of this invention to provide a method for identifying an elective replacement indicator voltage for an implantable electrochemical cell which reduces the likelihood of premature or tardy device replacement of the cell when powering a device.

According to the present invention, therefore, a method for providing an elective replacement indicator voltage for an implantable electrochemical cell is provided comprising the step of first providing an exemplary electrochemical cell comprised of an anode; a cathode of a first cathode active material different than a second cathode active material, the first cathode active material being of a first energy density and a first rate capability and the second cathode active material being of a second energy density and a second rate capability, wherein the first cathode active material is contacted to one side of a current collector and facing the anode with the second cathode active material positioned on the opposite side of the current collector, and wherein the first energy density of the first cathode active material is less than the second energy density of the second cathode active material while the first rate capability of the first cathode active material is greater than the second rate capability of the second cathode active material; and an electrolyte activating the anode and the cathode.

When such an exemplary electrochemical cell has been provided, the method further comprises the steps of repeatedly connecting and disconnecting the exemplary electrochemical cell to a sequence of at least three loads, thereby discharging the exemplary electrochemical cell from a state of about zero percent depth-of-discharge to at least about ninety percent depth-of-discharge while measuring cell voltage; generating cell voltage vs. depth-of-discharge data plots for the at least three loads repeatedly connected to the exemplary electrochemical cell; and identifying a range of depths-of-discharge for the at least three loads wherein a statistical indicator of the variability of the cell voltage with load at the same depth-of-discharge is less than a predetermined value among all of the at least three loads.

The statistical indicator may simply be the range of the cell voltages, i.e. the maximum cell voltage minus the minimum cell voltage from among the at least three cells at the same depth-of-discharge. Alternatively, the statistical indicator may be the variance of the cell voltages, or the standard deviation of the cell voltages at the same depth-of-discharge.

The elective replacement indicator voltage for the implantable electrochemical cell is then defined as the cell voltage that occurs at a predetermined load at a specified point within the identified range for the exemplary electrochemical cell, wherein the implantable electrochemical cell is substantially identical to the exemplary electrochemical cell. The predetermined load is preferably in the range of the upper and lower limits, inclusive, of the at least three loads. The specified point may be the lower limit of the range, or some point along the range, such as the midpoint of the range, or ¾ of the range, or even the upper limit of the range. The particular point selected will depend upon the details of the application.

Instead of providing a single exemplary cell, an alternate embodiment includes the provision of at least three exemplary electrochemical cells. Each of the three exemplary electrochemical cells are connected to a separate load, wherein each of the separate loads are unequal. This embodiment of the method further includes the steps of generating cell voltage vs. depth-of-discharge data plots for the at least three exemplary electrochemical cells, and identifying a range of depths-of-discharge for the at least three exemplary electrochemical cells wherein a statistical indicator of the variability of the cell voltage with load at the same depth-of-discharge is less than a predetermined value among all of the at least three exemplary electrochemical cells.

The elective replacement indicator voltage for the implantable electrochemical cell is then defined as the cell voltage that occurs at a predetermined load at a specified point within the identified range for the at least three exemplary electrochemical cells, wherein the implantable electrochemical cell is substantially identical to the exemplary electrochemical cells.

In an alternative embodiment, following the step of discharging the exemplary cell or cells and obtaining discharge data, one may run a numerical simulation to expand the spectrum of loads considered in identifying the depths-of-discharge range, followed by the identification of the depths-of-discharge range.

There is further provided a method for providing an elective replacement indicator voltage for an implantable medical device comprising any of the combinations of steps recited herein for providing an elective replacement indicator voltage for an implantable electrochemical cell; providing the implantable medical device; and powering the implantable medical device with the implantable electrochemical cell. The implantable medical device may be comprised of a housing and control circuitry contained inside the housing to control functioning of the medical device. Implantable devices for which the foregoing methods are applicable include cardiac defibrillators, neurostimulators, and pacemakers.

The foregoing and additional objects, advantages, and characterizing features of the present invention will become increasingly more apparent upon a reading of the following detailed description together with the included drawings.

BRIEF DESCRIPTION OF THE DRAWINGS

The present invention will be described by reference to the following drawings, in which like numerals refer to like elements, and in which.

Figure 1:
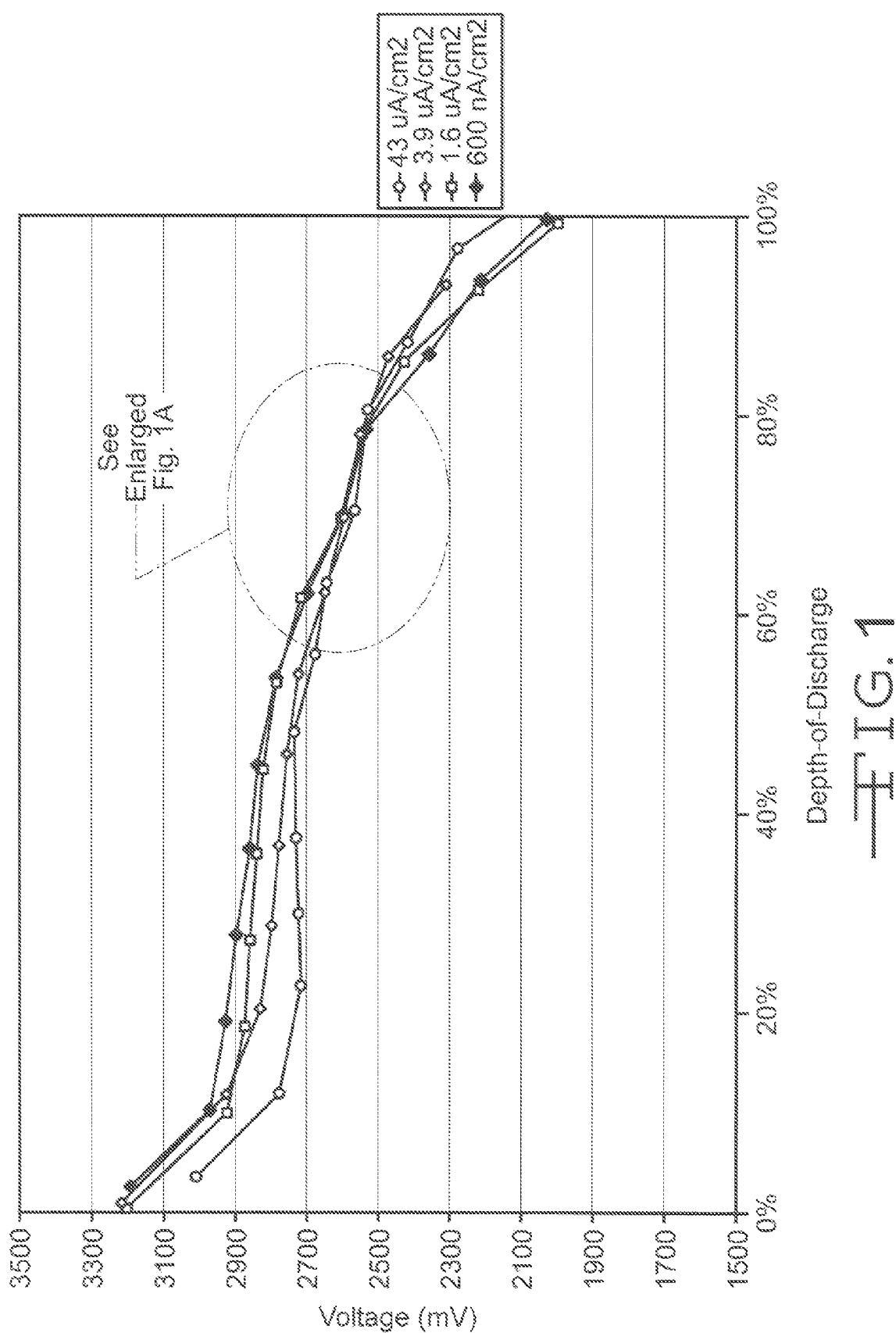
FIG. 1 is a plot of discharge curves for four exemplary $SVO:CF_x$ composite cathode-containing cells as described in the example provided herein.

The present invention will be described in connection with preferred embodiments, however, it will be understood that there is no intent to limit the invention to the embodiments described. On the contrary, the intent is to cover all alternatives, modifications, and equivalents as may be included within the spirit and scope of the invention as defined by the appended claims.

DETAILED DESCRIPTION OF THE PREFERRED EMBODIMENTS

For a general understanding of the present invention, reference is made to the drawings. In the drawings, like reference numerals have been used throughout to designate identical elements.

In describing the present invention, a variety of terms are used in the description. As used herein, a "discharge curve" for an electrochemical cell is a plot of the cell voltage versus time as the cell is discharged by connection to a "load." As used herein, a "load" on an electrochemical cell is simply a resistance that results in a particular current being supplied by the cell. As used herein, the term "depth-of-discharge" The term percent of depth-of-discharge (DOD) is defined as the ratio of delivered capacity to theoretical capacity times 100.

A particular depth-of-discharge, or "state of charge" is a point along the discharge curve of a cell. As used herein, "end of life" with respect to an electrochemical cell is the point along the discharge curve of a cell at which the cell is considered incapable of powering a particular device such that the device functions properly. End of life of a cell thus occurs before the cell is at 100 percent depth-of-discharge.

The present invention pertains to a primary electrochemical cell, and a method of selecting a replacement indicating voltage to avoid the aforementioned problems with the waste of energy in replacing the cell too early in its life, or with the risk to a patient in replacing the cell too late in its life. One embodiment of the invention is the application of this method to an electrochemical system with a lithium anode and a cathode composed of a mixture of silver vanadium oxide and carbon monofluoride. Specifically, in a preferred embodiment, the invention is directed to using a replacement indicating voltage range wherein the cell voltage varies by less than about 150 millivolts when the current is adjusted between 100 nanoamperes/cm$^2$ and 100 microamperes/cm$^2$ of cathode surface area. This corresponds to a cell voltage of 2.53V to 2.72V for the SVO:CF$_x$ system. The invention enables more precise determination of the replacement point, thereby reducing the likelihood of either premature or tardy cell replacement.

In general, the anode of the inventive cell is an alkali metal and the cathode could be composed of any material capable of accepting alkali metal ions at a voltage greater than 2.0V relative to the anode. In one preferred embodiment, the anode is lithium and the cathode is composed of SVO and CF$_x$ combined in one of various ways. For example, the cathode could be comprised of at least one layer of SVO material and one layer of CF$_x$ material either intimately contacted or separated by a porous current collector that allows ion migration between the two layers. Potential configurations of such cathodes include SVO/current collector/CF$_x$, SVO/current collector/CF$_x$/SVO, SVO/current collector/CF$_x$/current collector/SVO. Alternatively, the SVO and CF$_x$ may be mixed.

Because this invention deals with a replacement indicating voltage determined under primarily thermodynamic conditions, the observations made with respect to the exemplary system will pertain to any cell with an SVO and CF$_x$ composite cathode regardless of the cathode design. Changes in the relative amount of SVO and CF$_x$ will change the shape of the discharge curve of the particular cell, but the state-of-charge of the individual materials will be identical for a given voltage and load. For this reason, the invention is not specific to the depth-of-discharge for any particular material ratio of SVO to CF$_x$. For a mixed cathode system, the depth-of-discharge of the identified range from which the elective replacement indicator voltage is selected will vary depending on the material ratio. It is to be understood that the present invention is applicable to all material ratios.

During the discharge of the cell, the impact of the load on the voltage may change. At a particular state-of-charge (i.e. a point along the cell discharge curve or a point in the cell life), the voltage may be highly sensitive to the load, whereas it may be insensitive to the load at another state-of-charge. In an implantable medical device, it is desirable to define a replacement voltage near the end of the cell life at a state-of-charge where the cell voltage changes minimally with load. The method of the present invention provides an advantage in medical devices because the load applied by the device can depend on a variety of factors and may not be predictable or accurately known. The load may also change depending on the functions the device is performing or the needs of the patient. It is desirable, therefore, to identify a range along the depth-of-discharge curve over which the cell voltage is approximately constant with respect to load near the end of life of the cell, and to select the elective replacement indicating voltage from within that range.

Selecting within the range and thus eliminating the load dependence of the voltage prevents premature replacement of the cell that would be otherwise triggered by periods of heavy battery load resulting from increased levels of device function. Also, undesirably late replacement indication can be prevented in the case where the device draws unusually low power levels. A delayed replacement indication can result in loss of device function prior to replacement, with potentially serious consequences for the patient depending on the type of device and the nature of its function.

In one embodiment of the method, the ERI voltage is located at a state-of-charge wherein the cell voltage varies by less than 150 millivolts when the load dependent current is varied from between 100 nanoamperes/cm$^2$ of cathode surface area and 100 microamperes/cm$^2$ of cathode surface area.

The method of the present invention may be illustrated with reference to the following example. A set of four substantially identical exemplary Li/SVO/CF$_x$ electrochemical cells (i.e. within the capabilities of tooling, and laboratory equipment and practices) were fabricated as follows:

A set of cathode assemblies was prepared, each by pressing approximately 337 mg of CF$_x$ material in a matrix of binder and conductive additive between two titanium screens. Approximately 246 mg of silver vanadium oxide material in a matrix of binder and conductive additive was pressed on both sides of the assembly to provide a cathode having the configuration SVO/screen/CF$_x$/screen/SVO. The percentage of capacity of this cathode from SVO is 35%, and from CF$_x$, 65%. The total surface area of each cathode assembly was 15 cm$^2$. Each assembly was heat-sealed inside a polyethylene separator.

Each cell assembly was comprised of six cathode assemblies. Each of the cathode assemblies was combined with an anode prepared from a lithium metal ribbon applied to a nickel current collector. The lithium thickness was 0.0069 inches. Each anode was heat-sealed in a polyethylene separator, and each cell assembly was placed in a hermetic stainless steel can filled with an electrolyte consisting of 1M LiAsF$_6$ in propylene carbonate:1,2-dimethoxyethane mixed 1:1 by volume.

When cell fabrication was complete, each of the cells was connected to a different variable resistor such that each cell was discharged at 37° C. under a different load. Variable resistors were used so that as the voltage of the cells decreased during discharge, the resistances could be varied to maintain the load at constant current. The four exemplary cells were each discharged at 600 nA/cm$^2$, 1.6 µA/cm$^2$, 3.9 µA/cm$^2$, and 43 µA/cm$^2$. Voltage values were measured during the discharge of each of the cells from zero to nearly 100 percent depth-of-discharge.

Figure 1A:
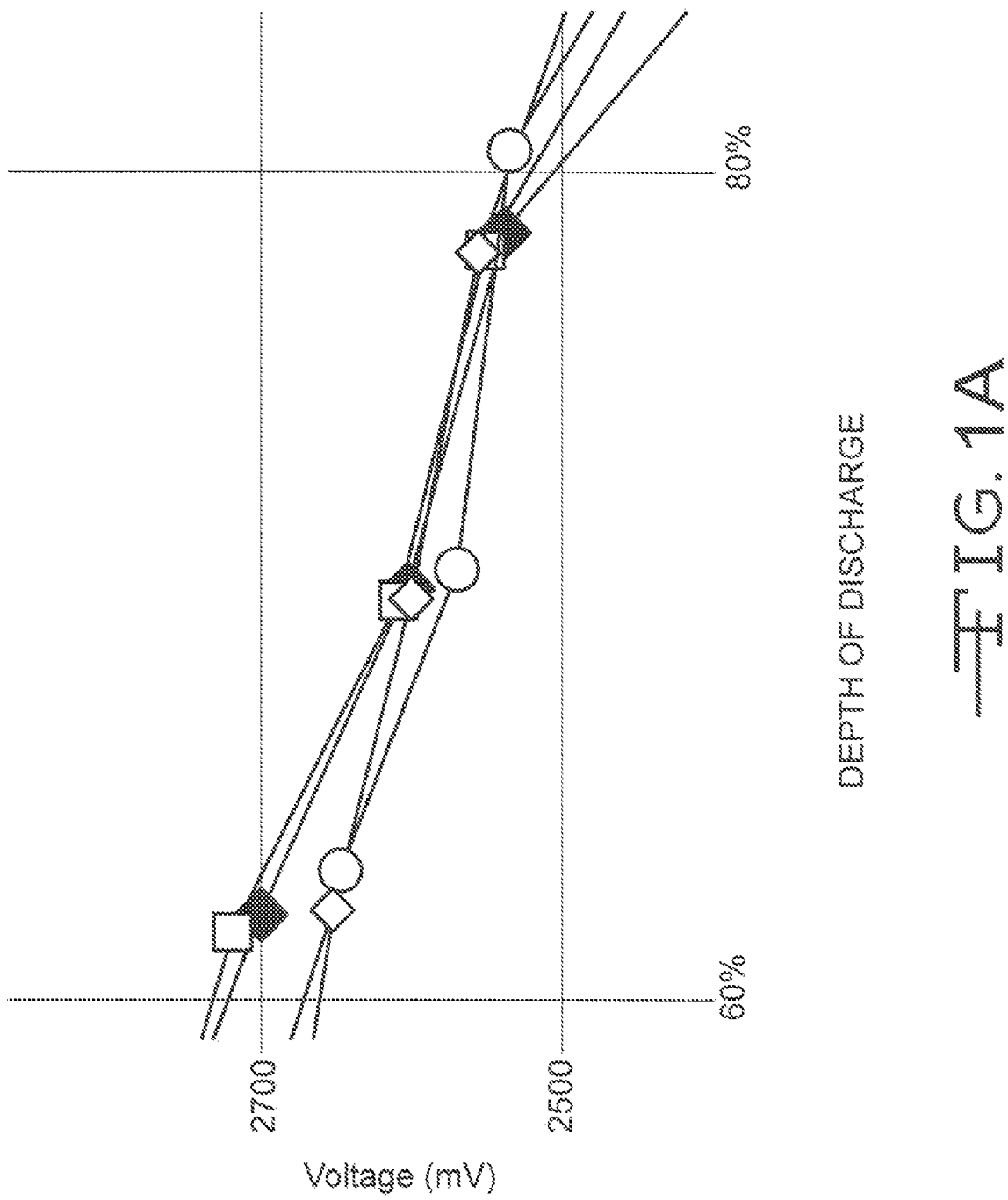
FIG. 1A is a detailed view of a portion of the plot of FIG. 1 over a range where the variation in cell voltage with depth-of-discharge is small.

FIG. 1 is a plot of discharge curves for four exemplary SVO:CF$_x$ composite cathode-containing cells discharged through the four different loads. The capacity delivered by each cell was divided by the theoretical capacity to provide the % depth-of-discharge (DOD) on the x-axis. This also normalizes the discharge curves with respect to time, as the length of time of discharge for each cell varies inversely with the applied load. FIG. 1A is a detailed view of a portion of the plot of FIG. 1 over a range where the variation in cell voltage with depth-of-discharge is small.

The variability of the effect of the load applied to the cells on the cell voltage is readily apparent. In the range of about 10% to about 50% of depth-of-discharge, the cell voltage varies widely and is highly dependent on the discharge load. In the range of 60 to 80% depth-of-discharge, the discharge curves converge considerably, indicating that the cell voltage is less dependent on the discharge load in that region. Table 1 depicts data selected from this depth-of-discharge range, as well as the 40% depth-of-discharge data.

TABLE 1

| | CELL VOLTAGES (mV) | | | |
|---|---|---|---|---|
| LOAD | 40% DOD | 60% DOD | 70% DOD | 80% DOD |
| 600 nA/cm$^2$ | 2856 | 2724 | 2590 | 2534 |
| 1.6 µA/cm$^2$ | 2836 | 2732 | 2604 | 2514 |
| 3.9 µA/cm$^2$ | 2775 | 2672 | 2575 | 2500 |
| 43 µA/cm$^2$ | 2730 | 2656 | 2590 | 2520 |
| RANGE | 126 | 48 | 29 | 34 |
| STANDARD DEVIATION | 50 | 19 | 10 | 14 |

It can be seen that at about 40% depth-of-discharge, the range of cell voltages is about 2,730 millivolts for the 600 nA/cm$^2$ load to about 2,860 millivolts for the 43 µA/cm$^2$ load. The standard deviation of the four cell voltages is about 50 millivolts. In the 60% to 80% depth-of-discharge, the variation of cell voltages is considerably less, with the voltage range (i.e. maximum voltage–minimum voltage) less than 50 millivolts and the standard deviation less than 20 millivolts for all loads. Thus, if one were to choose the statistical indicator of voltage range, and a maximum acceptable range of voltage variation of 50 millivolts, the range of depth-of-discharge from which the ERI voltage could be selected would be from about 60% to about 83% depth-of-discharge. If the maximum acceptable range was 35 millivolts, the depth-of-discharge range would be about 68% to about 80% depth-of-discharge.

In like manner, if one were to choose the statistical indicator of standard deviation, and a maximum acceptable standard deviation of 20 millivolts, the range of depth-of-discharge from which the ERI voltage could be selected would also be from about 60% to about 83% depth-of-discharge.

After the range of depths-of-discharge has been identified, the ERI voltage for the implantable electrochemical cell is then defined as the cell voltage that occurs at a predetermined load at a specified point within the identified range for the exemplary electrochemical cell. The predetermined load is preferably in the range of the upper and lower limits, inclusive, of the at least three loads. The specified point in the identified depths-of-discharge range may be the lower limit of the range, or some point along the range, such as the midpoint of the range, or ¾ of the range, or even the upper limit of the range. The particular point selected will depend upon the details of the application, including the total time to end-of-life of the cell, and the degree of risk allowable when delaying replacement further into the identified depth-of-discharge range. For example, if the cell were powering a life support device such as an implantable cardiac defibrillator wherein low risk would be important, and the range of 68% to 80% DOD were selected, one might choose the beginning of the range, i.e. 68% DOD. Referring to FIG. 1A, if 1 µA/cm$^2$ was chosen as the predetermined load, the ERI voltage would be about 2,600 millivolts.

It is not required that multiple cells be fabricated and tested at different loads in order to obtain the required data to identify the range of depths-of-discharge from which the ERI will be selected. In an alternate embodiment, a single exemplary cell may be provided, and the method may instead comprise the steps of repeatedly connecting and disconnecting the exemplary electrochemical cell to a sequence of at least three loads in order to obtain data which indicates the dependence of cell voltage on applied load. The data may then be plotted as shown in FIG. 1, thereby providing similar results and enabling the determination of the ERI voltage in a similar manner. For either method, it is not required that a steady discharge through the load be maintained. The cell may also be subjected to one or more pulsed discharges, which may be used to mimic device power demands.

Figure 2:
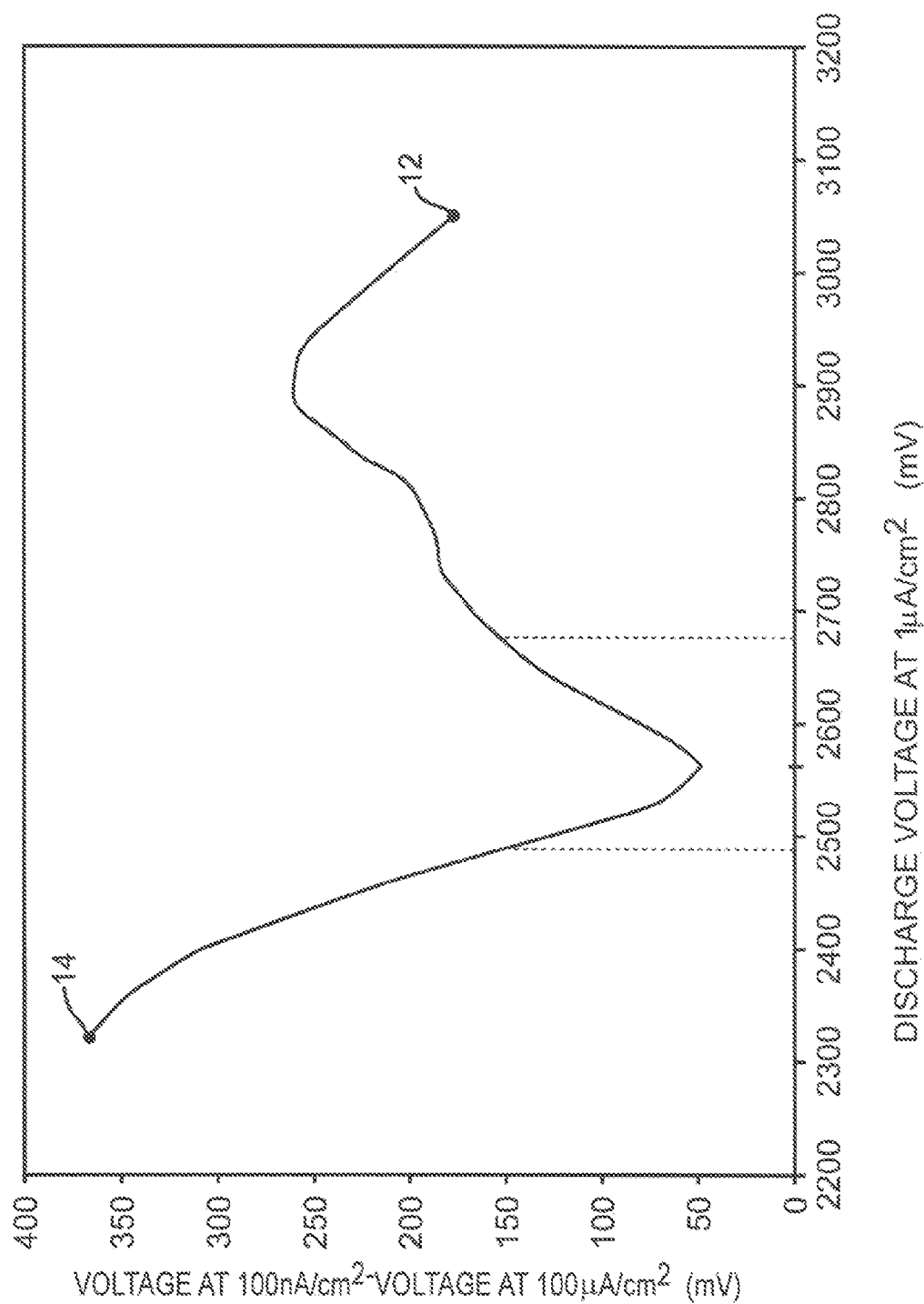
FIG. 2, is a plot of the calculated difference in voltage at a particular state-of-charge for the exemplary cells of FIG. 1 operating at a load of 100 $nA/cm^2$ and operating at a load of 100 $\mu A/cm^2$.

In another embodiment of the method, a numerical simulation is used to expand the spectrum of loads considered in identifying the depth-of-discharge range. The simulation may encompass a load spectrum of three orders of magnitude or more. FIG. 2 is a plot of such a simulation showing the exemplary Li/SVO/CFx cells of FIG. 1 subjected to a first load of 100 nA/cm$^2$ minus an identical cell having been subjected to a second load of 100 µA/cm$^2$ at a different time, versus the voltage had either one of the cells been subjected to a load of 1 µA/cm$^2$.

Point 12 on the plot is at zero percent depth-of-discharge, when the cell is new, and the voltage is nearly 3,100 mV at 1 µA/cm$^2$ load. Point 14 is at about 90% depth-of-discharge, and the voltage has decreased to about 2,300 mV at 1 µA/cm$^2$ load. It can be seen that early in the cell life (near point 12) and late in the cell life (near point 14), the voltage difference is quite large, and often exceeds 200 mV. The voltage difference is at a minimum of 50 mV at about 2,560 mV, and the regions on each side of this minimum have a relatively small dependence of cell voltage on load.

Referring again to FIG. 2, if the maximum acceptable voltage difference over the simulated load range was determined to be 150 mV, then the elective replacement indicating voltage should be selected from the range of about 2,490 mV to about 2,670 mV.

In contrast, if the ERI voltage was chosen to be 2,800 mV, this selection would place the cell at 9% depth-of-discharge under a load of 100 uA/cm$^2$ as opposed to 59% depth-of-discharge under a load of 100 nA/cm$^2$. Such an amount of variability is not desirable for an implantable device and could result in a significantly premature triggering of the replacement indicator if the replacement voltage is sampled too close to heavy current usages by the device. Alternatively, selection of a replacement voltage within the inventive range of, for example, 2,600 mV would result in a DOD of 60% at 100 uA/cm$^2$ versus a DOD of 74% at 100 nA/cm$^2$. The shift of 14% DOD is more desirable than the 50% shift described above for the non-inventive range.

In a further embodiment, one may perform an analysis which provides equations for the maximum and minimum depths-of-discharge that define the operative depth-of-discharge range.

In the case of the SVO and CF$_x$ mixed system, the replacement indicating point can be predicted by an equation which considers the ratio of SVO and CF$_x$ capacity in the cell. The minimum depth-of-discharge suitable for replacement indication is described by the following equation:

$$DOD_{Minimum} = 80.0 - 40.0 \times \frac{Capacity_{SVO}}{Capacity_{CFx} + Capacity_{SVO}}$$

The maximum depth-of-discharge suitable for replacement indication is described by the following equation:

$$DOD_{Maximum} = 89.6 - 16.1 \times \frac{Capacity_{SVO}}{Capacity_{CFx} + Capacity_{SVO}}$$

The DOD is defined as the delivered capacity divided by the total theoretical capacity of SVO and $CF_x$ in the cell. The capacity of SVO and $CF_x$ in the cell is defined as the mass of each active material multiplied by the theoretical gravimetric capacity of the corresponding material. The theoretical capacity of SVO is 315 mAh/g and the theoretical capacity of $CF_x$ is 875 mAh/g. The equations provide a range of DOD's in which the cell voltage varies by less than 150 mV when the current is adjusted between 100 nA/cm² of cathode surface area and 100 uA/cm² of cathode surface area. The minimum replacement point ($DOD_{minimum}$) is calculated to be 66.0% and the maximum replacement point ($DOD_{maximum}$) is calculated to be 84.0% using the equations above.

Figure 3:
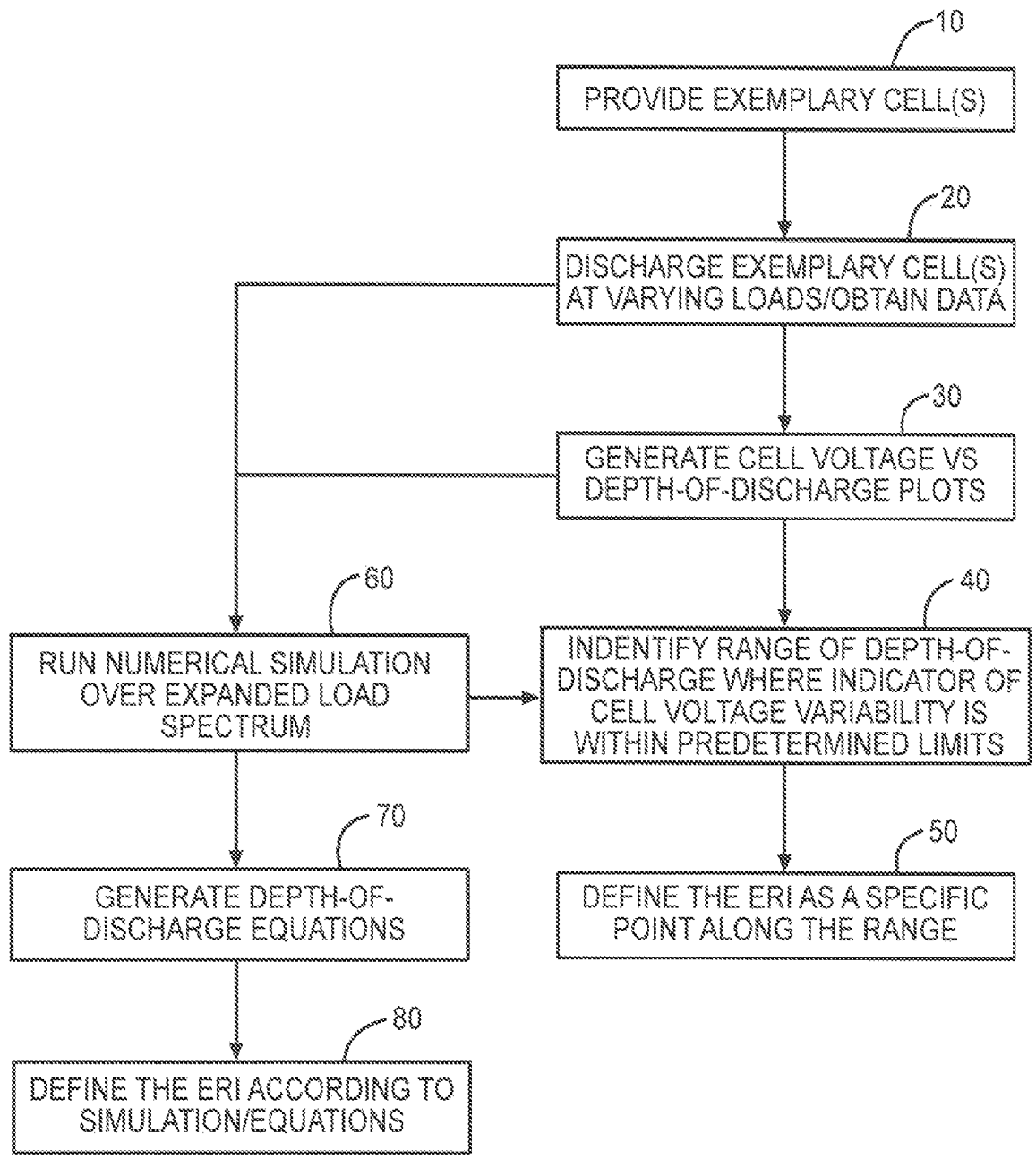
FIG. 3 is a flowchart that summarizes the steps in methods of the present invention for providing an elective replacement indicator voltage for an implantable electrochemical cell.

FIG. 3 is a flowchart that summarizes the steps for providing an ERI voltage for an implantable electrochemical cell. One embodiment of the method begins in step 10 with providing the exemplary electrochemical cell or cells as described previously. The exemplary cell(s) are then discharged using at least three different loads, and discharge data is collected in step 20. This data is used to generate cell voltage vs. depth-of-discharge plots for the various loads in step 30. From these plots, a range of depth-of-discharge for the various loads is identified in step 40, wherein a statistical indicator of the variability of the cell voltage with load is less than a predetermined value among all of the loads. The statistical indicator may be the range of the cell voltages, the variance of the cell voltages, or the standard deviation of the cell voltages. The ERI voltage for the implantable electrochemical cell is then defined in step 50 at a specified point within the identified range for the exemplary electrochemical cell.

Alternatively, following step 20 or step 30, one may perform a numerical simulation in step 60 to expand the spectrum or range of loads considered in identifying the depth-of-discharge range, followed by the identification of the depth-of-discharge range in step 40. Alternatively, one may generate equations for the maximum and minimum depths-of-discharge that define the operative depth-of-discharge range in step 70, and then define ERI voltage in accordance with the equations in step 80.

It is, therefore, apparent that there has been provided, in accordance with the present invention, a method for identifying an elective replacement indicator voltage for an implantable electrochemical cell. While this invention has been described in conjunction with preferred embodiments thereof, it is evident that many alternatives, modifications, and variations will be apparent to those skilled in the art. Accordingly, it is intended to embrace all such alternatives, modifications and variations that fall within the spirit and broad scope of the appended claims.

What is claimed is:

1. A method for providing an elective replacement indicator voltage for a first electrochemical cell intended as a power source for an implantable medical device, comprising the steps of:
   a) providing a second electrochemical cell that is substantially identical to the first cell, the second cell comprised of:
      i) an anode;
      ii) a cathode of a first cathode active material different than a second cathode active material, the first cathode active material being of a first energy density and a first rate capability and the second cathode active material being of a second energy density and a second rate capability, wherein the first cathode active material is contacted to one side of a current collector and facing the anode with the second cathode active material positioned on the opposite side of the current collector, and wherein the first energy density of the first cathode active material is less than the second energy density of the second cathode active material while the first rate capability of the first cathode active material is greater than the second rate capability of the second cathode active material; and
      iii) an electrolyte activating the anode and the cathode;
   b) repeatedly connecting and disconnecting the second cell to a sequence of at least three loads, thereby discharging the second cell from a state of about zero percent depth-of-discharge to at least about ninety percent depth-of-discharge while measuring cell voltage;
   c) generating cell voltage vs. depth-of-discharge data plots for the at least three loads to which the second cell is repeatedly connected;
   d) identifying a range of depth-of-discharge for the at least three loads, wherein a statistical indicator of the variability of the second cell voltage with load at the same depth-of-discharge is less than a predetermined value among all of the at least three loads; and
   e) defining the elective replacement indicator voltage for the first electrochemical cell as that cell voltage that occurs at a predetermined load at a specified point within the identified range for the second electrochemical cell.

2. The method as recited in claim 1, wherein the predetermined load is in the range of the upper and lower limits, inclusive, of the at least three loads.

3. The method as recited in claim 1, wherein the statistical indicator is the difference between the maximum cell voltage and the minimum cell voltage at the same depth-of-discharge.

4. The method as recited in claim 1, wherein the statistical indicator is the standard deviation of the cell voltages at the same depth-of-discharge.

* * * * *